United States Patent [19]

Miletich

[11] Patent Number: 5,112,331
[45] Date of Patent: May 12, 1992

[54] ORTHOPEDIC PINS FOR EXTERNAL FIXATOR

[76] Inventor: Vel Miletich, 917 Via Panorama, Palos Verdes Estates, Calif. 90274

[21] Appl. No.: 617,431

[22] Filed: Nov. 20, 1990

Related U.S. Application Data

[63] Continuation of Ser. No. 366,694, Jun. 15, 1989, abandoned.

[51] Int. Cl.$^5$ .............................................. A61B 17/56
[52] U.S. Cl. ........................................ 606/53; 606/59
[58] Field of Search .................. 606/53, 54, 55, 56, 606/57, 58, 59, 64, 71, 72; 411/451, 452, 490, 491; 63/3; 446/116

[56] References Cited

U.S. PATENT DOCUMENTS

| | | | |
|---|---|---|---|
| 377,805 | 2/1888 | Grant | 411/490 |
| 653,328 | 7/1900 | Tyden | 403/292 |
| 994,330 | 6/1911 | Morris | 411/453 |
| 1,912,222 | 5/1933 | Rosenberg | 411/453 |
| 1,994,422 | 3/1935 | Sasek | 606/59 |
| 2,055,024 | 9/1936 | Bittner, Jr. | 606/56 |
| 2,346,346 | 4/1944 | Anderson | 128/92 Z |
| 2,356,591 | 8/1944 | Jesionowski | 128/92 ZW |
| 2,497,626 | 2/1950 | Persall | 128/92 Z |
| 3,120,148 | 2/1964 | Prutton | 411/490 |
| 3,230,643 | 1/1966 | Mathus | 446/116 |
| 3,717,067 | 2/1973 | Vick | 411/490 |
| 3,719,342 | 3/1973 | Kupersmit | 411/490 |
| 3,977,397 | 8/1976 | Kalnberz | 128/92 Z |
| 4,373,518 | 2/1983 | Kaiser | 128/92 YE |
| 4,574,795 | 3/1986 | Georges | 128/92 YY |
| 4,615,338 | 10/1986 | Ilizarov | 128/92 ZY |
| 4,784,125 | 11/1988 | Monticelli | 120/92 Z |
| 4,829,787 | 5/1989 | Yoda | 63/3 |
| 4,869,242 | 9/1989 | Gulluzzo | 606/59 |
| 4,923,458 | 5/1990 | Fischer | 606/59 |

FOREIGN PATENT DOCUMENTS 3409070 9/1985 Fed. Rep. of Germany ........ 128/92 YY

OTHER PUBLICATIONS

Lagacy of an unpopular war, Article in Time Magazine, Special Ed., Apr. 10, 1989 pp. 64–65. Photograph Ilizarov External Fixator, Produced by Medical Plastic srl 1988, The Ilizarov External Fixator Product Information, pp. 1–20.

*Primary Examiner*—Robert A. Hafer
*Assistant Examiner*—Michael Brown
*Attorney, Agent, or Firm*—Poms, Smith, Lande & Rose

[57] ABSTRACT

An improved orthopedic pin for an external fixator has an enlarged diameter axial region wherein its diameter selected to be larger than a diameter of an osteal bore through which the pin is adapted to be disposed. A frustoconical section is adjacent each side of the enlarged region to form a bevelled surface on each side thereof which is at an angle sufficient to minimize insertion into the osteal bore while simultaneously reducing trauma to the soft tissue during insertion and removal of the pin.

2 Claims, 2 Drawing Sheets

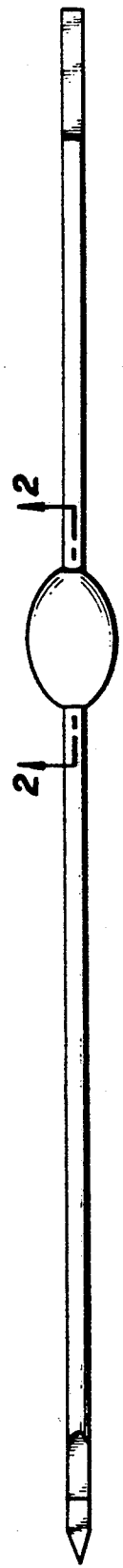
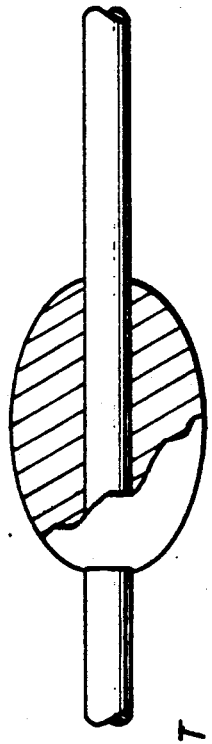
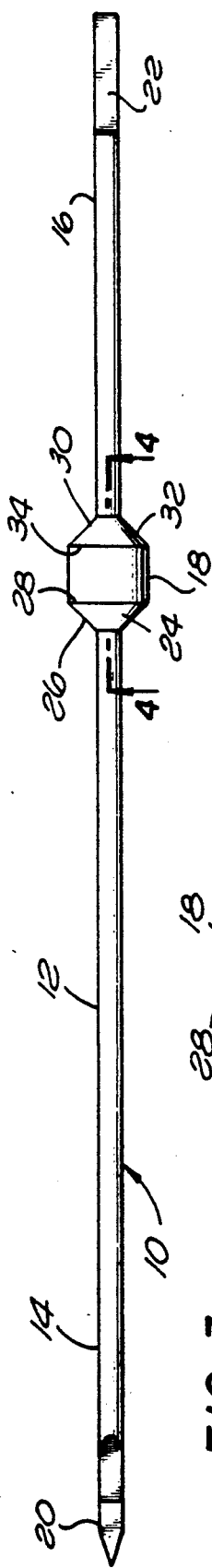
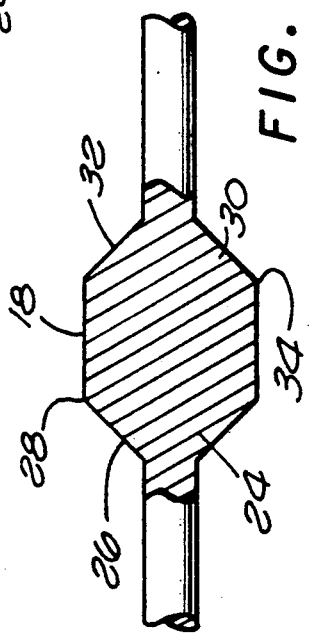
FIG. 1 PRIOR ART
FIG. 2 PRIOR ART
FIG. 3
FIG. 4

ORTHOPEDIC PINS FOR EXTERNAL FIXATOR

This is a continuation of copending application(s) Ser. No. 07,366,694 filed on Jun. 15, 1989 now abandoned.

BACKGROUND OF THE INVENTION

1. Field of the Invention

The present invention relates generally to medical apparatus and more particularly to an improved orthopedic pin and clamp for an external fixator.

2. Description of the Related Art

The ILIZAROV (TM) external fixator provides for the anatomical reduction of bone injuries requiring high stability of the bone fracture segments, and preservation of injured limb functions and early mobilization. For example, the ILIZAROV external fixator is typically used for open and closed fracture fixation pseudoarthroses of long bones (both congenital and acquired), limb lengthening by epiphyseal or metaphyseal distraction, correction of bone or soft tissue deformities, and correction of bone or soft tissue defects. The external fixator uses essentially a bloodless surgery technique, allows for the treatment of patients with complex diseases and bone defects that would otherwise have been unsuccessfully treated with traditional methods.

The main parts of the ILIZAROV external fixator are the standard elements used to correct skeletal deformities. These standard elements include wires, full rings, half rings, arches, wire fixation bolts, detachable wire fixation buckles and dual sided wire fixation buckles. Generally, the wires are fixed to the full rings and half rings of the wire fixation bolts at each of their ends after being passed through an osteal bore and the soft tissue in the limb of a patient.

The secondary parts of the fixator are necessary for the assemblage of the apparatus, namely threaded rods, telescopic rods, threaded rods with slots, connection plates, curve and twisted plates, supports and posts, hinges, washers, sockets, bushings, bolts and nuts. To assemble the numerous pieces of equipment, various types of wrenches and wire pinchers are needed. Additionally, various general orthopedic instruments are required such as chisels, hammers, pinchers and power drills to insert the wires. An exemplary assemblage of the external fixator is described in greater detail hereinbelow with reference to FIG. 9. A more detailed description of the external fixator is found in the Ilizarov et al., U.S. Pat. No. 4,615,338 for an Automatic Compression Distraction Apparatus.

Generally, the many elements of the external fixator provides great flexibility in use of the apparatus. For example, the wires may be inserted in many different directions at different levels of the effective limb, or adjustment of the rings permit reassembly or adjustment of the apparatus during the course of patient treatment. The proper position and orientation of bony segments are maintained to achieve continuous reduction. Also, the correction of the direction and type of forces that act on the bone during the course of treatment are allowed. Finally, the necessary degree of stability to allow early weight bearing and reduce complications during the course of treatment is obtained.

The wires can be introduced into the bone and fixed to the main and secondary supports of the fixator. A mechanical action of slow and gradual compression or distraction of bony segments is possible in many different directions. It is also possible to combine multiple treatment levels through the action of different wire placements. Fine precision movement as well as large forces of distraction are possible. During the course of patient treatment, the loads acting on the bone through the wires will have maximum stability and can be used to correct bony problems.

There are many advantages to the external fixator. Because the pins are small in diameter, the blood and nerve supplies including the intramedullary canal are not severely compromised. A further advantage is the minimization of further trauma to the anatomy and the gradual movement of the bony segments during the treatment process. Because of the tensioning effects of the pins, the bone is continuously loaded unlike a plate or any other type of internal fixation. The bony loading seen in the axial direction is one of a natural and uniformed nature. The blood supply is not compromised, and the bone is loaded by known biological laws of the natural frequency of magnitude. The tension wires are remarkably resistance and have enough elasticity so as to allow a proper biological stimulus to bone healing.

To allow the bony segments to be moved during the courses of treatment, some of the wires used in the external fixator include a stopper thereon as best seen in prior art FIGS. 1 and 2. The stopper abuts against the bone and allows the wires to be angulated in a variety of ways and positioned at any point along the fixation rings. By paying attention to vascular and nerve anatomy, the pins can be placed through the bone at different levels and angles. The bony segment to be moved under the tensioning of the wire.

In the prior art, the stopper is formed on selected ones of the pins by dropping a piece of solder thereon. The disadvantage and limitation of the use of the solder is that the heat dissipated by the molten solder onto the steel pin destroys the heat tempering of the pin. Since the solder abuts against the bone at the osteal bore, the disruption of the heat treatment may cause the pin to break at the solder. Furthermore, the solder itself may break off from the pin causing the bone to shift position on the pin negating the benefits of the treatment.

Another disadvantage and limitation of the above device is that when the pins are clamped to the rings, sheer forces are developed in the pin at the interface of the head of a bolt which clamps the pin down or at the edge of the ring itself. The sheer forces may cause the pins to break at this location.

SUMMARY OF THE INVENTION

Accordingly, it is an object of the present invention to overcome one or more of the disadvantages and limitations of the prior art enumerated hereinabove. It is another object of the present invention to provide an improved orthopedic pin for use in an external fixator. Yet another object of the present invention is to provide an improved clamp to minimize sheer forces on the orthopedic pins used in the external fixator.

According to the present invention, an orthopedic pin for an external fixator is constructed from a unitary piece of surgical steel. More specifically, the orthopedic pin has an elongated cylindrical body having a first end portion, a second end portion and in accordance with the present invention, an enlarged diameter axial region. The enlarged region has a diameter selected to be larger than the diameter of the osteal bore to which the pin is adapted to b disposed.

In a further embodiment of the present invention, the pin of unitary construction includes a first frustoconical region axially adjacent the enlarged region. The frustoconical region forms a bevelled surface extending from a first circumferential edge of the enlarged region to the pin. The bevelled surface has an angle from the axis of the pin selected to minimize trauma to soft tissue of the limb during insertion and further to minimize the depth of insertion of the frustoconical section into the osteal bore.

In still a further embodiment of the present invention, the pin includes a second frustoconical region axially adjacent the enlarged region. The second frustoconical region forms another bevelled surface extending from a second circumferential edge of the enlarged region. Again, the bevelled surface of the second frustoconical region forms an angle to the axis of the pin selected to minimize trauma to the soft tissue during removal of the pin.

The improved clamp of the present invention includes a bolt having a head portion and a threaded portion. The head portion has a V-shaped groove disposed proximate the threaded portion. When the bolt is secured to the ring by a nut, the end portion of the pin is received within the V-shaped groove. The pin has a planer surface disposed along a cord of a cross-section of the pin which abuts the face of the ring. The V-shaped groove provides a clamping force to the ring but minimizes sheer forces at the interface.

These and other objects, advantages and features of the present invention will become more apparent to those skilled in the art from a study of the following detailed description of an exemplary preferred embodiment when read in conjunction with the attached drawings and appended claims.

BRIEF DESCRIPTION OF THE DRAWINGS

FIG. 1 is an orthopedic pin of a type known in the prior art;

FIG. 2 is an enlarged portion, broken away and
partially in cross-section, of the prior art pin taken along line 2—2 of FIG. 1;

FIG. 3 illustrates an orthopedic pin constructed according to the principles of the present invention;

FIG. 4 is an enlarged portion, broken away and partially in cross-section, of the orthopedic pin taken
along line 4—4 of FIG. 3;

DESCRIPTION OF AN EXEMPLARY PREFERRED EMBODIMENT

Figure 5:
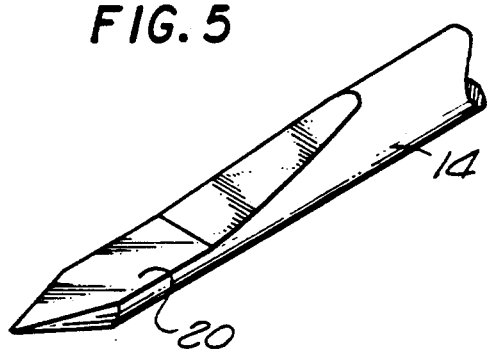
FIG. 5 is an enlarged portion broken away, of one end of the orthopedic pin of FIG. 3.

Referring now to FIGS. 3–6, there is shown an improved orthopedic pin 10 constructed according to the principles of the present invention. The pin 10 is of unitary construction and includes an elongated cylindrical body 12 having a first end portion 14, a second end portion 16, and an enlarged diameter axial region 18. The enlarged region 18 has a diameter selected to be larger than a diameter of an osteal bore through which the pin 10 is adapted to be disposed.

Figure 6:
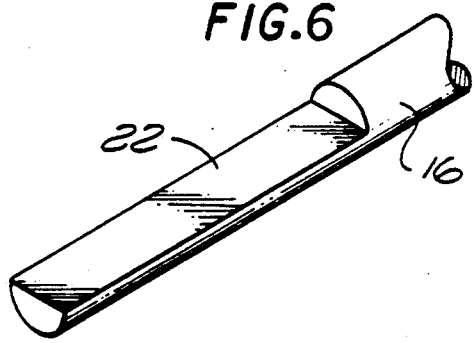
FIG. 6 is an enlarged portion, broken away, of the other end of the orthopedic pin of FIG. 3.

The first end portion 14 of the orthopedic pin 10 is constructed to form a trocar point 20, as best seen FIG. 5. The second end portion 16, is constructed to form an axially extending planar surface 22, as best seen in FIG. 6. The surface 22 is formed along a cord of a cross-section of the orthopedic pin 10.

In accordance with the further embodiment of the present invention, the orthopedic pin 10 includes a first frustoconical region 24 axially adjacent the enlarged region 18. The frustoconical region 24 forms a bevelled surface 26 extending from a first circumferential edge 28 of the enlarged region. The bevelled surface 26 forms an angle to the axis of the pin 10 selected to minimize trauma to soft tissue of a limb during insertion of the pin and further to minimize the depth of insertion of the frustoconical region 24 into an osteal bore.

In accordance with a further embodiment of the present invention, the pin 10 further includes a second frustoconical region 30 axially adjacent the enlarged region 18. The second frustoconical region 30 forms a second bevelled surface 32 extending from a second circumferential edge 34 of the enlarged region 18. The second bevelled surface 32 forms an angle to the axis of the orthopedic pin 10 selected to minimize trauma to soft tissue during removal of the pin.

Figure 7:
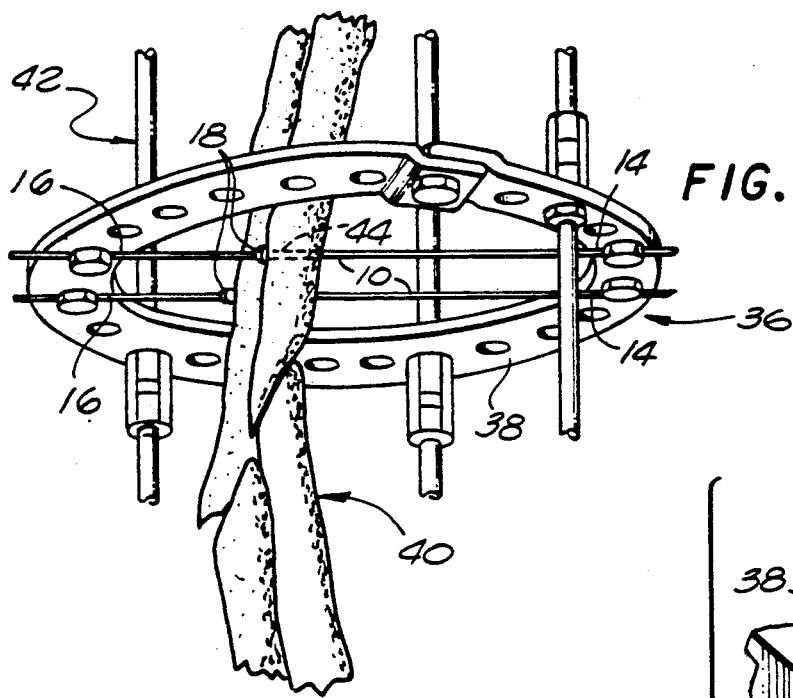
FIG. 7 shows an assembled external fixator incorporating the novel orthopedic pins constructed according to the principles of the present invention.
Figure 8:
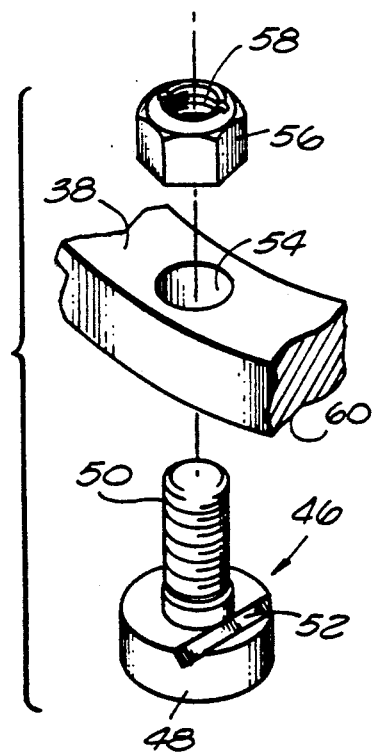
FIG. 8 is an exploded view of a clamp of the external fixator shown in FIG. 7.
Figure 9:
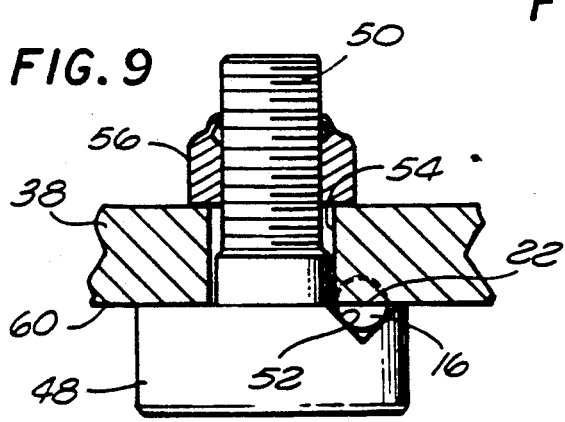
FIG. 9 shows a detail of the clamp of the external fixator of FIG. 6 affixing an orthopedic pin to the ring.

Referring now further to FIG. 7-9, there is shown an external fixator 36 having a plurality of rings 38 (one such ring 38 being shown) through which a limb, generally indicated at 40, of a patient is disposed. The external fixator 36 further includes means 42 for affixing the rings 38 to each other in a pre-determined orientation. As best seen in FIG. 7, the external fixator 36 also includes the orthopedic pins 10 extending through the limb 40. Each of the pins 10 are clamped at each end 14 and 16 to respective one of the rings 38 to maintain the limb in a fixed relationship to the rings 38.

The enlarged diameter axial region 18 is disposed adjacent the limb 40 at the osteal bore 44. As best seen in FIGS. 8 and 9, the improvement of the present invention further comprises a bolt 46 having a head portion 48 and a threaded portion 50. The head portion 48 has a V-shaped groove 52 disposed proximate the threaded portion 50. The rings 38 have an opening 54 dimensioned to receive threaded portion 50. In accordance therewith, the improvement further comprises a nut 56 having a threaded bore 58 adapted for engagement with the threaded portion 50 of the bolt 46. The V-shaped groove 52 is dimensioned to receive the second end portion 16 of the orthopedic pin 10. As best seen in FIG. 9, the planar surface 22 abuts a face 60 of the ring 38 when clamped thereto. The dimension of the V-shaped groove is such that it minimizes sheer forces upon the second end portion 16 of the orthopedic pin 10 while providing a firm engagement with the ring 38.

There has been described hereinabove improvements to the orthopedic pins used in an external fixator. Those skilled in the art may now make numerous uses of and departures from the present invention without departing from the inventive concepts disclosed herein. Accordingly, the present invention is to be defined solely by the scope of the appended claim.

What is claimed is:

1. A method of forming an orthopedic pin for an external fixator comprising the steps of:
    providing a cylindrical solid piece of metal having a first end, a second end, and a central portion;
    selecting a central portion diameter that is larger than a diameter of an osteal bore through which the pin is adapted to be disposed such that, after the pin is properly inserted, a portion of the central portion will abut the bone through which the pin is inserted;

forming the central portion into the selected central portion diameter;

forming the first and second ends into a diameter smaller than the selected central portion diameter; and selecting a first surface configuration from the axis of the pin to the central portion that will minimize trauma to soft tissue during insertion of the pin and minimize the depth of insertion of the central portion into the osteal bore; and forming a surface on the central portion of the pin adjacent the first end in the selected first configuration so as to form a first configured region on the central portion of the pin to provide an integral unitary high strength pin.

2. A method of forming an orthopedic pin for an external fixator comprising the steps of:

providing a cylindrical solid piece of metal having a first end, a second end, and a central portion;

selecting a central portion diameter that is larger than a diameter of an osteal bore through which the pin is adapted to be disposed such that, after the pin is properly inserted, a portion of the central portion will abut the bone through which the pin is inserted;

forming the central portion into the selected central portion diameter;

forming the first and second ends into a diameter smaller than the selected central portion diameter; and selecting a second surface configuration from the axis of the pin to the central portion that will minimize trauma to the soft tissue during removal of the pin; and forming a surface on the central portion of the pin adjacent the second end in the selected second configuration so as to form a second configured region on the central portion of the pin to provide an integral unitary high strength pin.

* * * * *